(12) United States Patent
Bradwell

(10) Patent No.: US 7,897,353 B2
(45) Date of Patent: Mar. 1, 2011

(54) METHOD OF DETECTING OR MONITORING A MALIGNANT PLASMA CELL DISEASE

(75) Inventor: Arthur R. Bradwell, Birmingham (GB)

(73) Assignee: The Binding Site Group Limited, Birmingham (GB)

( * ) Notice: Subject to any disclaimer, the term of this patent is extended or adjusted under 35 U.S.C. 154(b) by 196 days.

(21) Appl. No.: 11/883,003

(22) PCT Filed: Jan. 26, 2006

(86) PCT No.: PCT/GB2006/000267
§ 371 (c)(1),
(2), (4) Date: Jul. 25, 2007

(87) PCT Pub. No.: WO2006/079816
PCT Pub. Date: Aug. 3, 2006

(65) Prior Publication Data
US 2008/0166742 A1 Jul. 10, 2008

(30) Foreign Application Priority Data
Jan. 27, 2005 (GB) ................................ 0501741.3

(51) Int. Cl.
*G01N 33/53* (2006.01)
(52) U.S. Cl. .................................... 435/7.1; 530/387.1
(58) Field of Classification Search .................. 435/7.1; 530/387.1
See application file for complete search history.

(56) References Cited

U.S. PATENT DOCUMENTS

| 3,907,502 A | 9/1975 | Brink |
| 4,618,589 A | 10/1986 | Jefferis et al. |
| 5,185,066 A | 2/1993 | Golias |
| 2002/0182748 A1 | 12/2002 | Reardon |
| 2004/0018576 A1 | 1/2004 | DeMatteo et al. |

FOREIGN PATENT DOCUMENTS

| EP | 0291194 B2 | 2/1994 |
| WO | WO97/17372 | 5/1997 |
| WO | WO2005/116651 | 12/2005 |

OTHER PUBLICATIONS

Pappas et al, 1985, Clin Immunol Immunopathology, 34: 392-396.*
Shimizu et al, 1982, Clin Exp Immunol, 50: 596-600.*
Briault et al, 1988, Clin Exp Immunol, 74: 182-184.*
Whicher et al, 1987, Clin Chem. 33/10: 1771-1773.*
Beaume et al, 1994, Blood, 84(4): 1216-1219.*
Jones et al, 1991, Clin Chem, 37(11): 1922-1926.*
Chersi et al, 2000, Human Immunology, 61: 1298-1306.*
International Search Report and Written Opinion for PCT/GB2006/000267 filed May 24, 2006.
Abraham, R.S., et al., "Light Chain Myeloma: Correlation of Serum Nephelometric Analysis For the Quantitation of Immunoglobulin Free Light Chain With urine Bence Jones Protein" (abstract) presented at AACC Chicago, IL 2001, *Clinical Chemistry*, vol. 47, No. S6, pp. A33.
Anonymous: "Serum and Urine Protein Electrophoresis (SPE/UPE", Internet Article, Oct. 12, 2004, URL:http://web.archive.org/web/20041012055838/http://www.bindingsite.co.uk/electrophoresis.asp.
Bradwell, Arthur R., et al., "Highly Sensitive, Automated Immunoassay For Immunoglobulin Free Light Chains In Serum And Urine", 2001, *Clinical Chemistry*, vol. 47, No. 4, pp. 673-680.
Bradwell, Arthur R., et al., "Serum Free Light Chain Immunoassays And Their Clinical Application", 2002, *Clinical and Applied Immunology Reviews*, vol. 3, pp. 17-33.
Bradwell, Arthur R., et al., "Serum Test For Assessment Of Patients With Bence Jones Myeloma", Feb. 8, 2003, *The Lancet (Reprint)*, vol. 361, No. 9356, pp. 489-491.
Bradwell, Arthur R., "Clinical Applications Of Serum Free Light Chain, Immunoassays", Nov. 2003, pp 1-4, reprinted from CLI, available at http://www.bindingsite.co.uk/files/CLI.pdf.
Bradwell, Arthur R., "Serum Free Light Chain Analysis", 2004, $2^{nd}$ Edition, *The Binding Site Ltd.*, ISBN: 07044 24541, pp. 15-16 Fig. 3.4 on p. 16, and Text on p. 15.
Bradwell, Arthur R., "Serum Free Light Chain Analysis", 2004, $2^{nd}$ Edition, *The Binding Site Ltd.*, ISBN: 07044 24541, Chapters 4, 5, and 6, pp. 23-62.
Chui, Shiu Hon, et al., "Light-Chain Ratio Of Serum IgA1 In IgA Nephropathy", 1991, *Journal of Clinical Immunology*, vol. 11, No. 4, pp. 219-223.
Haraldsson, A., et al., "Determination Of Kappa And Lambda Light Chains In Serum Immunoglobulins G, A and M", 1991, *Ann. Clin. Biochem*, vol. 28, pp. 461-466.
Drayson, Mark, et al., "Serum Free Light-Chain Measurements For Identifying And Monitoring Patients With Nonsecretory Multiple Myeloma", May 1, 2001, *Blood*, vol. 97, No. 9, pp. 2900-2902.

(Continued)

*Primary Examiner*—Misook Yu
*Assistant Examiner*—Minh-Tam Davis
(74) *Attorney, Agent, or Firm*—Barnes & Thornburg LLP

(57) ABSTRACT

A method of detecting or monitoring a malignant plasma cell disease comprising detecting in a sample the ratio between the relative amounts of immunoglobulins having: (i) a heavy chain class bound to λ light chains; and (ii) immunoglobulins having the same heavy chain class but bound to κ light chains. Preferably the ratio is determined by (1) a method wherein the ratio is determined using: (i) an antibody, or a fragment thereof, having specificity for a heavy chain class at the same time as having specificity for a first light chain in combination with either: (ii) an antibody, or a fragment thereof, having specificity for the heavy chain class at the same time as having specificity for the second light chain; or (iii) an antibody, or fragment thereof, having specificity for the heavy chain and a further antibody, or fragment thereof, having specificity for the second light chain. (2) a method wherein the ratio is determined using: (i) at least one antibody, or a fragment thereof, specific for the heavy chain class; (ii) an antibody, or a fragment thereof, specific for λ light chains; and (iii) an antibody, or a fragment thereof, specific for κ light chains; or Antibodies specific for a heavy chain class at the same time as having specificity for a specific light chain are also provided.

7 Claims, 10 Drawing Sheets

OTHER PUBLICATIONS

Katzmann, Jerry A., et al., "Serum Reference Intervals And Diagnostic Ranges For Free κ and Free λ Immunoglobulin Light Chains: Relative Sensitivity For Detection Of Monoclonal Light Chains", 2002, *Clinical Chemistry*, vol. 48, No. 9, pp. 1437-1444.

Lachmann, Helen J., et al., "Outcome In Systemic AL Amyloidosis In Relation To Changes In Concentration Of Circulating Free Immunoglobulin Light Chains Following Chemotherapy", 2003, British Journal Of Haematology, vol. 122, pp. 78-84.

Mead, G.P., et al., "Serum Free Light Chain Immunoassays As An Aid In The Diagnosis And Monitoring Of Light Chain Monoclonal Gammopathies", Oct. 2001, pp. 239 (abstract) Proceedings of the Joint Annual Meeting of HSANZ and ASBT.

Mead, G.P., et al., "Nephelometric Measurement Of Serum Free Light Chains In Nonsecretory Myeloma", 2002, *Clin Chem*, vol. 48, No. 6 (abstract), Presented at the AACC, FL.

Mead, G.P., et al., "Serum Free Light Chains For Monitoring Multiple Myeloma", 2004, Blackwell Publishing Ltd, *British Journal of Haematology*, vol. 126, pp. 348-354.

Nakano, Takanari, et al., "ELISAs For Free Human Immunoglobulin Light Chains In Serum: Improvement Of Assay Specificity By Using Two Specific Antibodies In A Sandwich Detection Method", 2004, *Journal of Immunological Methods*, vol. 293, pp. 183-189.

Sirohi, Bhawana, et al., "Multiple Myeloma", 2004, *The Lancet*, vol. 363, pp. 875-887.

Prior M. et al, "Quantitation Of IgGkappa And IgGlambda In Normal And Pathological Sera," Protides Of The Biological Fluids, vol. 29, 1981, pp. 785-788.

Jefferis R. et al, "Quantitation Of Human Total IgG, Kappa lgG And Lambda IgG In Serum Using Monoclonal Antibodies," Journal Of Immunological Methods, vol. 39, No. 4, Dec. 28, 1980, pp. 355-362.

Derverill et al, "Monoclonal Antibodies To Human IgG: Reaction Characteristics In The Centrifugal Analyzer," Clinical Chemistry, vol. 27/12, 1981, pp. 2044-2047.

* cited by examiner

Figure 5. Standard curves for (a) IgA$_1$κ and (b) IgA$_1$λ
(a)
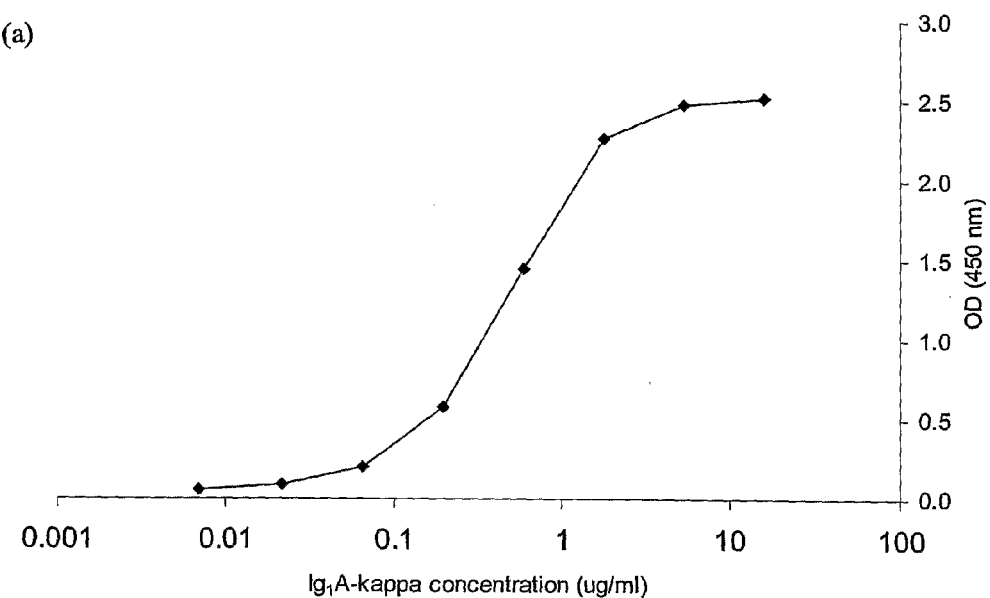
(b)
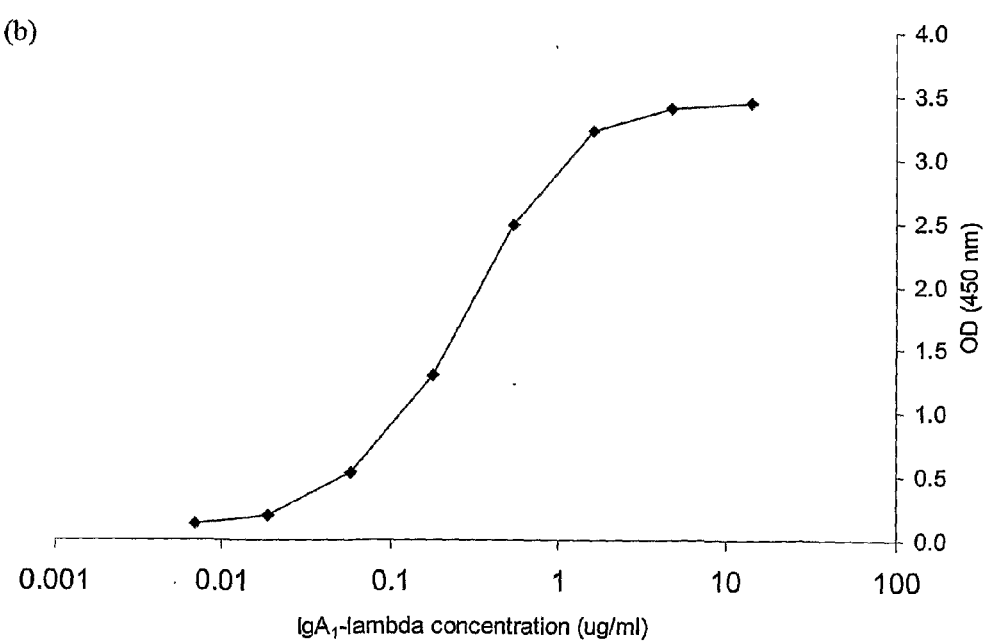

SPE scores: +++; +; +/-; -; -; -; -; -; -; -; -; -; ?; +++

No SPE scores

SPE scores: All - (negative)

SPE scores: +; +/-; -; -; -; -; -; +++

SPE scores: ++; ++; +/-?; +/-?; +/-?; -; -; -; -

SPE scores: All unclear. May all be negative

METHOD OF DETECTING OR MONITORING A MALIGNANT PLASMA CELL DISEASE

CROSS-REFERENCE TO RELATED APPLICATIONS

This application is a U.S. national counterpart application of international application serial no. PCT/GB2006/000267 filed Jan. 26, 2006, which claims priority to British application serial no. 0501741.3 filed Jan. 27, 2005.

FIELD OF INVENTION

The invention relates to assays and methods for detecting or monitoring malignant plasma cell disease, and to antibodies, or fragments of antibodies, which are specific for immunoglobulins, the immunoglobulins comprising a light chain bound to a heavy chain, the isolated antibody or fragment being further characterised by having specificity for a heavy chain class (also know as heavy chain class) and at the same time having specificity for a light chain type. Compositions and methods of using the antibodies, for example in the detection of a malignant plasma cell disease, such as a myeloma, are also provided.

BACKGROUND

Antibody molecules (also known as immunoglobulins) have a twofold symmetry and are composed of two identical heavy chains and two identical light chains, each containing variable and constant domains. The variable domains of the heavy and light chains combine to form an antigen-binding site, so that both chains contribute to the antigen-binding specificity of the antibody molecule. The basic tetrameric structure of antibodies comprises two heavy chains covalently linked by a disulphide bond. Bach heavy chain is in turn attached to a light chain, again via a disulphide bond. This produces a substantially "Y"-shaped molecule. This is shown schematically in FIG. 1.

Heavy chains are the larger of the two types of chain found in antibodies, with typical molecular mass of 50,000-77,000 Da, compared with the smaller light chain (25,000 Da).

There are five main classes or class s or classes of heavy chain which are γ, α, μ, δ and ε which are the constituents heavy chains for: IgG, IgA, IgM, IgD and IgE respectively. IgG is the major immunoglobulin of normal human serum, accounting for 70-75% of the total immunoglobulin pool. This is the major antibody of secondary immune responses. It forms a single tetramer of two heavy chains plus two light chains.

IgM accounts for approximately 10% of the immunoglobulin pool. The molecules, together with J-chains, form a pentamer of five of the basic 4-chain structures. The individual heavy chains have a molecular weight of approximately 65,000 and the whole molecule has a molecular weight of about 970,000. IgM is largely confined to the intravascular pool and is the predominant early antibody.

IgA represents 15-20% of human serum immunoglobulin pool. More than 80% of IgA occurs as a monomer. However, some of the IgA (secretory IgA) exists as a dimeric form.

IgD accounts for less than 1% of the total plasma immunoglobulin.

IgE, although scarce in normal serum, is found on the surface membrane of basophils and mast-cells. It is associated with allergic diseases such as asthma and hay-fever.

In addition to the five main classs or classes, there are four subclasses for IgG (IgG1, IgG2, IgG3 and IgG4). Additionally there are two subclasses for IgA (IgA1 and IgA2).

There are two types of light chain: Lambda (λ) and Kappa (κ). There are approximately twice as many κ as λ molecules produced in humans, but this is quite different in some mammals. Each chain contains approximately 220 amino acids in a single polypeptide chain that is folded into one constant and one variable domain. Plasma cells produce one of the five heavy chain types together with either κ or λ molecules. There is normally approximately 40% excess free light chain production over heavy chain synthesis. Where the light chain molecules are not bound to heavy chain molecules, they are known as "free light chain molecules". The κ light chains are usually found as monomers. The λ light chains tend to form dimers.

There are a number of proliferative diseases associated with antibody producing cells. FIG. 2 shows the development of B-cell lineage and associated diseases. These diseases are known as malignant plasma cell diseases. They are summarised in detail in the book "Serum-free Light Chain Analysis" A. R. Bradwell, available from The Binding Site Limited, Birmingham, UK (ISBN: 07044 24541).

In many such proliferative diseases a plasma cell proliferates to form a monoclonal tumour of identical plasma cells. This results in production of large amounts of identical immunoglobulins and is known as a monoclonal gammopathy.

Diseases such as myeloma and primary systemic amyloidosis (AL amyloidosis) account for approximately 1.5% and 0.3% respectively of cancer deaths in the United Kingdom. Multiple myeloma is the second-most common form of haematological malignancy after non-Hodgkin lymphoma. In Caucasian populations the incidence is approximately 40 per million per year. Conventionally, the diagnosis of multiple myeloma is based on the presence of excess monoclonal plasma cells in the bone marrow, monoclonal immunoglobulins in the serum or urine and related organ or tissue impairment such as hypercalcaemia, renal insufficiency, anaemia or bone lesions. Normal plasma cell content of the bone marrow is about 1%, while in multiple myeloma the content is typically greater than 30%, but may be over 90%.

AL amyloidosis is a protein conformation disorder characterised by the accumulation of monoclonal free light chain fragments as amyloid deposits. Typically, these patients present with heart or renal failure but peripheral nerves and other organs may also be involved.

There are a number of other diseases which can be identified by the presence of monoclonal immunoglobulins within the blood stream, or indeed urine, of a patient. These include plasmacytoma and extramedullary plasmacytoma, a plasma cell tumour that arises outside the bone marrow and can occur in any organ. When present, the monoclonal protein is typically IgA. Multiple solitary plasmacytomas may occur with or without evidence of multiple myeloma. Waldenström's macroglobulinaemia is a low-grade lymphoproliferative disorder that is associated with the production of monoclonal IgM. There are approximately 1,500 new cases per year in the USA and 300 in the UK. Serum ISM quantification is important for both diagnosis and monitoring. B-cell non-Hodgkin lymphomas cause approximately 2.6% of all cancer deaths in the UK and monoclonal immunoglobulins have been identified in the serum of about 10-15% of patients using standard electrophoresis methods. Initial reports indicate that monoclonal free light chains can be detected in the urine of 60-70% of patients. In B-cell chronic lymphocytic leukaemia monoclonal proteins have been identified by free light chain immunoassay.

Additionally, there are so-called MGUS conditions. These are monoclonal gammopathy of undetermined significance. This term denotes the unexpected presence of a monoclonal intact immunoglobulin in individuals who have no evidence of multiple myeloma, AL amyloidosis, Waldenström's macroglobulinaemia, etc. MGUS may be found in 1% of the population over 50 years, 3% over 70 years and up to 10% over 80 years of age. Most of these are IgG- or IgM-related, although more rarely IgA-related or bi-clonal. Although most people with MGUS die from unrelated diseases, MGUS may transform into malignant monoclonal gammopathies.

In at least some cases for the diseases highlighted above, the diseases present abnormal concentrations of monoclonal immunoglobulins or free light chains. Where a disease produces the abnormal replication of a plasma cell, this often results in the production of more immunoglobulins by that type of cell as that "monoclone" multiplies and appears in the blood.

The identification of monoclonal immunoglobulins, and the heavy and light chains making up those immunoglobulins may be carried out in a number of ways. Serum protein electrophoresis (SPE) and immunofixation electrophoresis (IFE) have been used for a number of years to identify the presence of monoclonal proteins in the serum. Serum protein electrophoresis is the standard method for screening for intact immunoglobulin multiple myeloma and is based upon scanning gels in which serum proteins have been separated, fixed and stained. There are limitations associated with this method, including that some samples from patients with myelomas appear normal by electrophoresis. This results in the possibility of missing patients and misdiagnosis of the disease. Furthermore, the technique does not readily allow for the accurate quantitative determination of the various proteins identified, particularly at low concentrations. Serum electrophoresis can be used to identify the presence of free light chains, but the detection limit is between 500 mg/L and 2,000 mg/L, depending upon whether or not the monoclonal protein migrates alongside β proteins. Sermon protein electrophoresis is negative for free light chains in all patients with non-secretory myeloma.

Immunofixation electrophoresis uses a precipitating antibody against the immunoglobulin molecules. Whilst this improves the sensitivity of the test it cannot be used to quantify monoclonal immunoglobulins because of the presence of the precipitating antibody. Immunofixation electrophoresis is also rather laborious to perform and interpretation may be difficult. Capillary zone electrophoresis is used in many clinical laboratories for serum protein separation and is able to detect most monoclonal immunoglobulins. However, when compared with immunofixation, capillary zone electrophoresis fails to detect monoclonal proteins in 5% of samples. These so-called "false negative" results encompass low-concentration monoclonal proteins.

Total κ and λ assays have been produced. However, total κ and total λ assays are too insensitive for the detection of monoclonal immunoglobulin or free light chain. This is due to high background concentrations of polyclonal bound light chains which interfere with such assays.

More recently, the applicants have developed a sensitive assay that can detect the free κ light chains and separately, the free λ light chains. This method uses a polyclonal antibody directed towards either the free κ or the free λ light chains. This is discussed in detail in the book by A. R. Bradwell. The possibility of raising such antibodies was also discussed as one of a number of different possible specificities, in WO 97/17372. This document discloses methods of tolerising an animal to allow it to produce desired antibodies that are more specific than prior art techniques could produce. The free light chain assay uses the antibodies to bind to free λ or free κ light chains. The concentration of the free light chains is determined by nephelometry or turbidimetry. This involves the addition of the test sample to a solution containing the appropriate antibody in a reaction vessel or cuvette. A beam of light is passed through the cuvette and as the antigen-antibody reaction proceeds, the light passing through the cuvette is scattered increasingly as insoluble immune complexes are formed. In nephelometry, the light scatter is monitored by measuring the light intensity at an angle away from the incident light, whilst in turbidimetry light scatter is monitored by measuring the decrease in intensity of the incident beam of light. A series of calibrators of known antigen (i.e. free κ or free λ) concentration are assayed initially to produce a calibration curve of measured light scatter versus antigen concentration.

This form of assay has been found to successfully detect free light chain concentrations. Furthermore, the sensitivity of the technique is very high.

Because a monoclonal plasma cell of the type causing e.g. multiple myeloma will produce only one type of antibody with a λ or a κ light chain, the relative ratio of λ or κ will change.

If the amount of the free λ light chain and the amount of the free κ light chain are known, it is possible to calculate the ratio between the free λ and the free κ light chains. An example of the results of plotting serum λ versus serum κ concentrations for patients with different diseases is shown in FIG. 3. The amount of free λ and free κ is skewed away from the normal concentrations because of the monoclonal nature of many of these diseases.

Measuring the κ:λ ratio for free light chains assists in the diagnosis of the disease. Furthermore, if the disease is treated, for example by chemotherapy or radiotherapy, the technique allows the disease to be monitored. If the disease is successfully being treated, then the concentrations of free light chains, which have a relatively short life span within the blood, will change and move more towards the normal concentrations observed for normal sera. Moreover, in malignant plasma cell diseases there is often suppression of production of the opposite light chain, so the κ:λ ratio can be more sensitive than individual FLC measurements.

Haraldsson A., et al. (Ann. Clin. Biochem (1991), 28(5): 461-466) discloses ELISA assays for the determination of kappa and lambda ratios within total IgG, IgA and IgM.

Chui S.A., et al. (J. Clin. Immunol. (1991), 11(4): 219-223) discloses studying patients with primary IgA nephropathy with an ELISA kit. The ELISA uses monoclonal mouse anti-human IgA1 as a solid phase capture and peroxidase-labelled anti-kappa and anti-lambda antibodies. IgA nephropathy is a kidney disease caused when IgA builds up as deposits in kidneys and appears to run in families.

FIG. 4 indicates that not all such diseases produce free light chains. The use of free light chains as a marker for the diseases is therefore not 100% successful.

SUMMARY

The inventors realised that it is possible to produce antibodies and assays that would be able to distinguish between, for example, IgG λ and IgG κ. They therefore tried to produce antibodies which are specific for immunoglobulins and which had specificity for both a heavy chain class and a light chain type. They have successfully been able to do this. They have also produced assays that allow the rapid quantitative measurement of, e.g. IgGλ and IgGκ ratios to allow the rapid identification and/or follow the progression of monoclonal diseases associated with production of a specific heavy chain class, or even heavy chain subclass, in conjunction with a bound λ or κ chain.

By determining the composition of immunoglobulins using an antibody specific to a heavy chain class at the same time as a light chain type or by using a first antibody against a heavy chain class and a second antibody to determine the light chain type bound to the heavy chain the inventors have produced a sensitive assay for malignant plasma cell diseases. The assays developed allow more sensitive monitoring of the diseases than, for example, by SPE. The greater sensitivity allows the detection of the clone, for example, when concentrations of the monoclonal protein have fallen below SPE detection limits. Furthermore, this has the potential to identify some biclonal diseases, which may have normal light chain ratios.

Moreover, a further advantage is that this assay should not be affected by renal function. Free λ and free κ are cleared by filtration through the kidneys and their concentration is affected by filtration rate. Due to its size, intact immunoglobulin is cleared by other mechanisms. Thus, rising levels of free light chain but no change in the amount of the immunoglobulins detected by the current invention may be used to indicate changes in renal clearance only, especially if the κ:λ ratio showed no changes.

Assays used include ELISA, nephalometry, turbidimetry and flow cytometry. However, the invention is not limited to such assays.

DETAILED DESCRIPTION

A first aspect of the invention provides a method of detecting or monitoring a malignant plasma cell disease comprising detecting in a sample the ratio between the relative amounts of immunoglobulins having:

(i) a heavy chain class bound to λ light chains; and
(ii) immunoglobulins having the same heavy chain class but bound to κ light chains.

The method preferably quantitatively measures the amounts of the two immunoglobulins in the sample.

Preferably, the sample is obtained from tissue or fluid, such as blood or serum from blood of an animal, such as a mammal, preferably a human. Additionally, it may be possible to identify such proteins in urine. Preferably the sample is assayed in vitro.

The class detected may be selected from IgA, IgG, IgM, IgD and IgE. The antibodies may also be subclass specific.

The inventors have found that it is possible to use single antibodies to discriminate between different heavy chain class/light chain type immunoglobulins. Hence, the method of the invention may be determined using:

(i) an antibody, or a fragment thereof, having specificity for a heavy chain class at the same time as having specificity for a first light chain type in combination with either:
(ii) an antibody, or a fragment thereof, having specificity for the heavy chain class at the same time as having specificity for the second light chain type; or
(iii) an antibody, or fragment thereof, having specificity for the heavy chain and a further antibody, or fragment thereof, having specificity for the second light chain type.

In an alternative aspect of the invention, two different parts of the immunoglobulin to be detected are bound by the antibodies used in the assay. One antibody binds a part of the heavy chain responsible for heavy chain class determination. The second-binds a part of the light chain responsible for identifying it as a κ, or λ chain.

Hence, preferably the ratio is determined using:
(i) at least one antibody, or a fragment thereof specific for the heavy chain class,
(ii) an antibody, or a fragment thereof, specific for λ light chains; and
(iii) an antibody, or a fragment thereof, specific for κ light chains.

The presence of the specific antibodies bound to these immunoglobulins may be determined using a labelled second antibody. For example, the binding antibody may be a sheep antibody. The immunoglobulins detected may be human immunoglobulins. Hence the presence of sheep antibodies bound to the human immunoglobulin may be determined using anti-sheep antibodies, e.g. from rabbit or horse.

Use of such antibodies allows the clones produced by the malignant plasma cell diseases to be characterised, even though they may not produce different ratios of free light chains. Furthermore, instead of just measuring free λ or free κ, this test is more specific because it identifies the heavy chain class as well. This improves the characterisation of the monoclonal plasma cell.

Results produced by the inventors indicate that some tumours which do not produce abnormal free κ to free λ ratios, can be identified because of the difference in the ratio of, for example, IgGκ and IgGλ or IgAκ and IgAλ observed.

Measurement of the heavy chain-light chain specific pair is capable of being automated. Furthermore, the technique is more sensitive and allows the quantitative determination of the amount of different immunoglobulins. It can be used both to aid diagnosis of a disease and also to monitor the response of the disease to treatment.

The antibodies used in the assay may be heavy chain subclass specific. For example, anti-IgA (IgA1 and IgA2) and anti-IgG (such as IgG1, IgG2, IgG3 or IgG4) antibodies are made by The Binding Site, Birmingham, United Kingdom. This gives more detailed knowledge of the disease being detected.

Polyclonal antibodies are preferably used. This allows an improved assay to be produced to monitor different immunoglobulins of, for example, the same class. Polyclonal antibodies allow some variability between different heavy chains of the same class to be detected because they are raised against a number of parts of the heavy chain.

The method of the invention may also be used using one or more of the following methods wherein the binding of the antibodies to the immunoglobulins in the sample is determined by using a nephelometer, a turbidimeter, flow cytometry, ELISA or fluorescently labelled beads such as Luminex™ beads. Alternatively, a microarray assay may be produced using the antibodies.

Preferably the ratio is determined by immunoassay, most preferably via an immunosorbent assay such as ELISA (Enzyme Linked Immunosorbent Assay). ELISA-type assays per se are well known in the art. They use antibodies, or fragments of antibodies, to detect blood groups, cell surface markers, drugs and toxins. In the case of the current invention, this type of assay has been used for the method of the invention.

The inventors have found that it is possible to produce ELISA assays at least as sensitive as Serum Protein Electrophoresis and, in at least some cases, more sensitive than using Immunofixation Electrophoresis (IFE), FREELITE™ (The Binding Site, Birmingham, UK) or obtaining total heavy chain class concentration as nephelometry.

ELISA uses antibodies to detect specific antigens. One or more of the antibodies used in the assay may be labelled with an enzyme capable of converting a substrate into a detectable analyte. Such enzymes include horseradish peroxidase, alkaline phosphatase and other enzymes known in the art. Alternatively, other detectable tags or labels may be used instead of, or together with, the enzymes. These include radioisotopes, a wide range of coloured and fluorescent labels known in the art, including fluorescein, Alexa fluor, Oregon Green, BODIPY, rhodamine red, Cascade Blue, Marina Blue, Pacific Blue, Cascade Yellow, gold; and conjugates such as biotin (available from, for example, Invitrogen Ltd, United Kingdom). Dye sols, metallic sols or coloured latex may also be used. One or more of these labels may be used in the ELISA assays according to the various inventions described herein, or alternatively in the other assays, labelled antibodies or kits described herein.

The construction of ELISA-type assays is itself well known in the art. For example, a "binding antibody" specific for the immunoglobulin is immobilised on a substrate. In this case, the immunoglobulin comprises a heavy chain of a particular class, or subclass, attached to either a λ light chain or κ light chain. The "binding antibody" may be immobilised onto the substrate by methods which are well known in the art. Immunoglobulins in the sample are bound by the "binding antibody" which binds the immunoglobulin to the substrate via the "binding antibody".

Unbound immunoglobulins may be washed away.

In ELISA assays the presence of bound immunoglobulins may be determined by using a labelled "detecting antibody" specific to a different part of the immunoglobulin of interest than the binding antibody.

Preferably, flow cytometry is used to detect the binding of the immunoglobulins of interest and measure the ratios. This technique is well known in the art for, e.g. cell sorting. However, it can also be used to detect labelled particles, such as beads, and to measure their size. Numerous text books describe flow cytometry, such as Practical Flow Cytometry, 3rd Ed. (1994), H. Shapiro, Alan R. Liss, New York, and Flow Cytometry, First Principles (2nd Ed.) 2001, A. L. Given, Wiley Liss.

One of the binding antibodies, such as the antibody specific for the heavy chain class, is bound to a bead, such as a polystyrene or latex bead. The beads are mixed with the sample and the second detecting antibody, such as antibody specific for λ light chains. The detecting antibody is preferably labelled with a detectable label, which binds the immunoglobulin to be detected in the sample. This results in a labelled bead when the immunoglobulin to be assayed is present.

Labelled beads may then be detected via flow cytometry. Different labels, such as different fluorescent labels may be used for, for example, the anti-λ and anti-κ antibodies. This allows the amount of each type of immunoglobulin bound to be determined simultaneously and allows the rapid identification of the κ:λ ratio for a given heavy chain class.

Alternatively, or additionally, different sized beads may be used for different antibodies, for example for different class specific antibodies. Flow cytometry can distinguish between different sized beads and hence can rapidly determine the amount of each heavy chain class in a sample.

Flow cytometry allows rapid identification of the κ/λ ratios for a given heavy chain class or subclass. This also reduces the need to do immunofixation tests.

An alternative method uses the antibodies bound to, for example, fluorescently labelled beads such as commercially available Lunminex™ beads. Different beads are used with different antibodies. Different beads are labelled with different fluorophore mixtures, thus allowing the λ/κ ratio for a particular heavy chain class or subclass to be determined by the fluorescent wavelength. Luminex beads are available from Luminex Corporation, Austin, Tex., United States of America.

The monoclonal proteins in a sample may be further characterised by looking at the amount of free λ or free κ light chains in the sample. This is preferably carried out using antibodies specific for free λ or free κ light chains, such as those sold under the trade mark FREELITE by The Binding Site Ltd, Birmingham, UK.

A further aspect of the invention provides an immunosorbent assay kit such as an ELISA assay kit, for use in a method according to any preceding claim comprising:
(i) at least one antibody, or a fragment thereof, specific for the heavy chain class;
(ii) an antibody, or a fragment thereof, specific for λ, light chains; and
(iii) an antibody, or a fragment thereof, specific for κ light chains.

The antibodies, labels, etc. are preferably as described above.

Preferably the antibody specific for the heavy chain class is immobilised to a substrate. The substrate may be a bead, but preferably is a microtitre plate well.

One or more of the antibodies preferably comprises a detectable label.

One or more controls, such as a known amount of a predetermined monoclonal protein, such as IgAλ or IgAκ, or a fragment thereof, may be provided in this and indeed other ELISA, flow cytometry, Luminex, microarrays or other assays described herein. The fragments, when used will retain, e.g. antigenic determinants for detecting class or light chain type.

Flow cytometry kits and Luminex beads are also provided comprising:
(i) at least one antibody, or a fragment thereof, specific for the heavy chain class;
(ii) an antibody, or a fragment thereof, specific for λ light chains; and
(iii) an antibody, or a fragment thereof, specific for κ light chains.

The arrangement of the antibodies, labels, etc. are preferably as described above.

Preferably the antibody specific for the heavy chain class is immobilised onto a substrate, such as a bead, and each type of light chain specific antibody (ii and iii) is labelled with a different detectable label.

Preferably the kit comprises a plurality of different antibodies, or fragments thereof, specific for different heavy chain classes, and each of the types of different heavy chain class antibodies is attached to a different size of bead.

Accordingly a further aspect of the invention provides isolated antibodies or fragments thereof which are specific for an immunoglobulin heavy chain-light chain pair, said isolated antibody or fragment thereof further characterised by having specificity for a heavy chain class and at the same time by having specificity for a light chain type.

Preferably, the antibody is a polyclonal antibody which is capable of binding to a heavy chain bound to a light chain, for example the tetramer containing two heavy chains and two light chains. Having specificity for a heavy chain class and specificity for a light chain class is intended to mean that the antibody is able to distinguish between different heavy chain classes and also is able to distinguish between heavy chains of the same class but which are bound to κ, or λ light chains. For example, the antibody is capable of distinguishing between IgGλ and IgGκ and is capable of distinguishing between IgGλ and IgAλ. Preferably, the antibody is specific for IgGλ, IgGκ, IgAλ, IgAκ, IgMλ, IgMκ, IgDλ, IgDκ, IgEλ or IgEκ.

The antibody may also be specific for a heavy chain subclass light chain combination of the class. For example, it may be specific for IgG1, IgG2, IgG3, IgG4, IgA1 or IgA2. That is, it is capable of distinguishing between IgG1κ and IgG2κ.

The fragments of the antibody are capable of specifically binding and detecting the heavy chain class and/or light chain type and may be a Fab or F(ab')$_2$ fragments.

Indeed, the fragments of antibody used in the other aspects of the invention may also be Fab or F(ab')$_2$ fragments.

Preferably, the antibody or fragment is a polyclonal antibody. Polyclonal antibodies allow a plurality of different antibodies to be raised against different epitopes for the specific heavy chain-light chain combination. This allows for the slight variations between different immunoglobulins, but which nevertheless comprise the same heavy chain-light chain combination.

The polyclonal antibodies used in the various aspects of the invention may be capable of being produced by the method shown in WO 97/17372. This allows the production of highly specific polyclonal antibodies.

The antibodies or fragments may be immobilised onto a substrate by techniques well-known in the art. The substrate may, for example, be a micro array or a microtiter plate. Alternatively, the substrate may be a polystyrene and/or latex bead. This allows the antibodies to be used in a number of different assays which are well-known in the art, for example as shown in EP 0291194 or ELISA assays. The antibody may also be labelled, for example, with a label described above for ELISA. This can be any entity, the presence of which can be readily detected. The label may be a visible label, that is an entity which, in its natural state, is readily visible either to the naked eye or with the aid of an optical filter and/or applied stimulation, such as UV light to produce fluorescence. For example, minute coloured particles, such as dye sols, metallic sols (e.g. gold) or coloured latex particles, may be used.

Indirect labels, such as enzymes (e.g. alkaline phosphatase and horseradish peroxidase) can be used, as can radioactive labels such as $^{35}$S.

Assays using antibodies are well-known in the art.

The antibodies may be used to produce flow cytometry or Luminex™ kits. These techniques are described herein. Preferably such kits comprise the antibody bound to a bead, such as polystyrene. Preferably the kit additionally comprises a labelled antibody for detecting the presence of immunoglobulins from a sample bound, via the antibody of the invention, to the bead.

Preferably the kit comprises two different types of antibodies specific for different heavy chain classes and/or different light chain types, and the different types of antibodies are supported on different sizes of beads and/or labelled with different detectable labels.

Kits for detection of specific immunoglobulin molecules comprising antibodies or fragments according to the invention are also provided.

The kits of the invention may additionally comprise antibodies specific for free λ or free κ, light chains.

The kits may additionally comprise one or more of: instructions for using the kit, substrate, a buffer, label, a preservative or a control.

Preferably, the immunosorbent assays, such as ELISA assays according to the various aspects of the invention comprise an antibody specific for λ light chains and a second specific for κ light chains, plus an antibody specific for the heavy chain class. Alternatively the ELISA comprises antibodies specific for the same heavy chain class, but different light chain types. Such assays may use, for example, a captive layer specific for the heavy chain class, such as IgG or IgA, plus detection antibodies (anti-λ and anti-κ). Alternatively, anti light-chain (e.g. anti-κ) may be used as a captive layer with a class specific antibody (e.g. anti-IgA).

The invention further provides a method of carrying out a specific binding assay, preferably in vitro, comprising:
  (i) providing a sample containing immunoglobulin molecules;
  (ii) contacting the sample with an antibody or a fragment thereof according to the invention; and
  (iii) detecting the specific binding of the antibody to an immunoglobulin molecule.

Preferably, the specific binding step (iii) is detected using a nephelometer or a turbidometer. As already indicated, such techniques are well-known in the art.

Alternatively, the specific binding assay may use an enzyme-linked immunosorbent assay (ELISA) to detect step (iii). Colorimetric methods of the detection of analytes to specific antibodies are known in the art. For example, EP 0291194 discloses immunoassays using test strips to detect various analytes. The document shows the production of such assays and the methods of detecting the analyte when bound to specific antibodies. Other techniques for producing assay devices are known in the art.

Preferably, the antibody or fragment thereof is immobilised on a solid support by techniques well-known in the art. The method may additionally provide the step of providing a labelling reagent capable of non-specific binding to the immunoglobulin molecule to be assayed and detecting the presence of the labelled immunoglobulin bound to the antibody or fragment. The labelling reagent may itself be another antibody directed against a different part of the immunoglobulin molecule, the separate antibody being labelled with a label, for example, of the sort discussed above. The presence of the label allows the production of, for example, a sandwich assay, and the identification of binding of the labelled immunoglobulin to the molecule to be assayed and its binding to the specific antibody according to the invention.

The methods of the invention further include ways of detecting the presence of a first immunoglobulin molecule having a specific class and having a specific light chain type comprising the use of an antibody or a fragment thereof according to the invention or a method according to the invention.

The amount of the immunoglobulin molecule may be quantitatively measured.

The methods may also further detect and quantify the presence of a second immunoglobulin molecule having the same specific heavy chain class as the first immunoglobulin molecule, but a different type of light chain is measured, for example using a different antibody according to the invention. This allows the ratio between the amounts of the first immunoglobulin molecule and the second immunoglobulin molecule to be determined, for example to identify the ratio between IgGλ and IgGκ. This allows the progression of a disease to be followed or alternatively the treatment of a disease to be followed.

The invention further comprises a method of diagnosing a malignant plasma cell disease in a patient comprising the use of an antibody or a fragment thereof according to the invention, or a method according to the invention. Preferably blood, urine or serum is assayed.

Preferably, the malignant plasma cell disease is selected from: multiple myeloma, AL amyloidosis, solitary plasmacytoma, extramedullary plasmacytoma, multiple solitary plasmacytomas, plasma cell leukaemia, Waldenström's macroglobulinaemia, B-cell non-Hodgkin lymphomas, B-cell chronic lymphocytic leukaemia or MGUS.

The invention will now be described by way of example only, with reference to the following figures:

BRIEF DESCRIPTION OF THE DRAWINGS

FIG. 5 shows standard curves for (a) IgA$_1$κ and (b) IgA$_1$λ for ELISA assays produced by the method described below:

FIG. 6 Patient No. 7148
FIG. 7 Patient No. 7273
FIG. 8 Patient No. 7283
FIG. 9 Patient No. 7255
FIG. 10 Patient No. 7401
FIG. 11 Patient No. 70236
FIG. 12 Patient No. 70338
FIG. 13 Patient No. 70382
FIG. 14 Patient No. 70392
FIG. 15 Patient No. 70052

Figure 1:
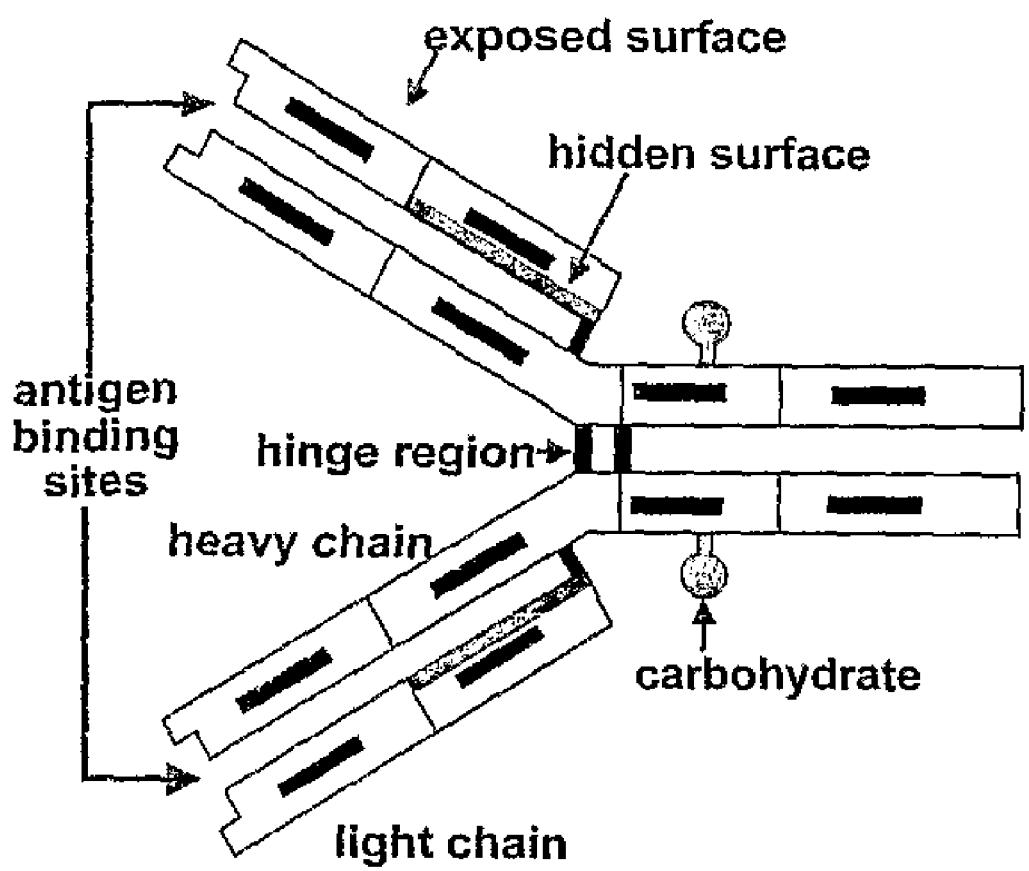
FIG. 1 shows a schematic diagram of an antibody.
Figure 2:
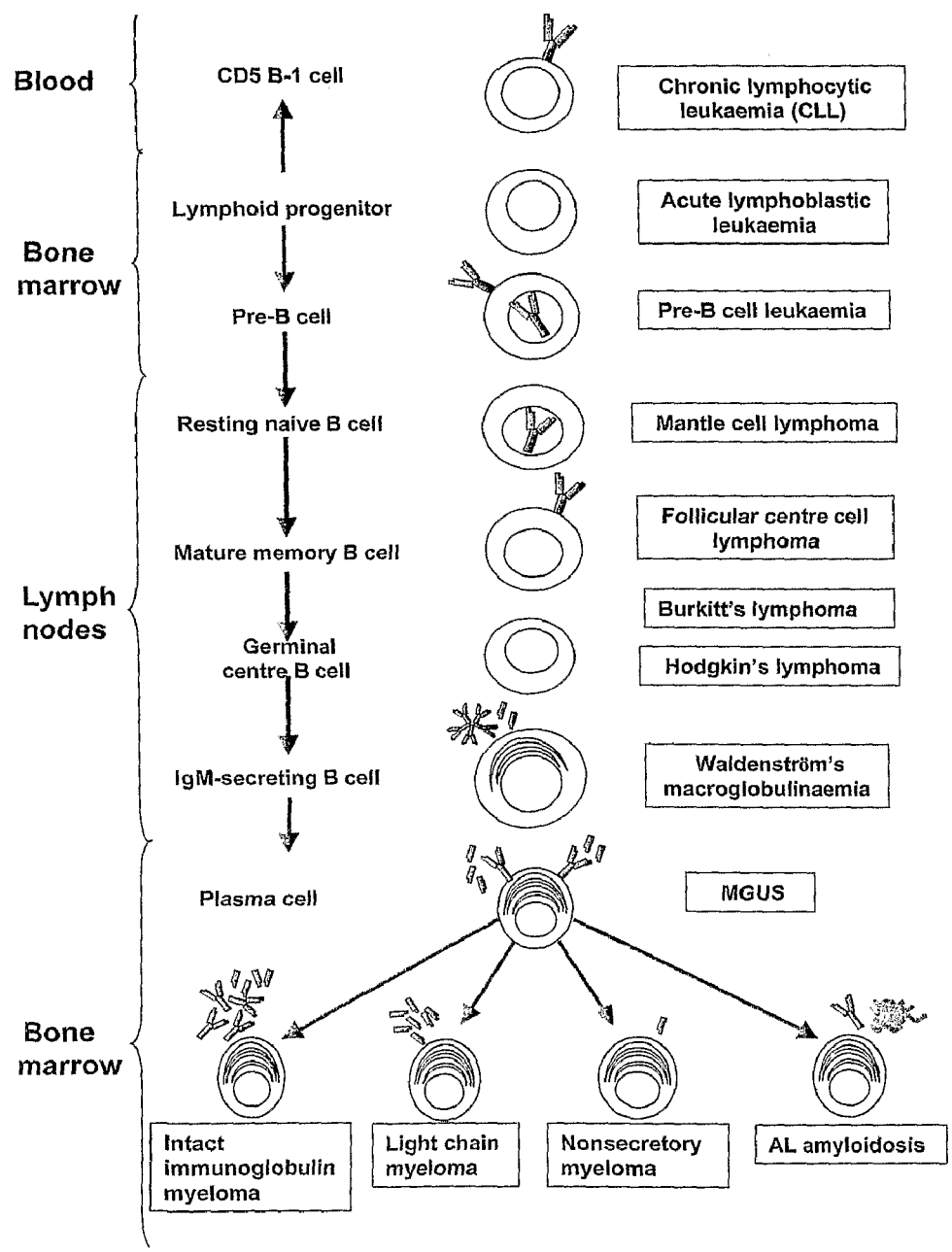
FIG. 2 shows the development of B-cell lineage and associated diseases. MGUS means monoclonal gammopathy of undetermined significance.
Figure 3:
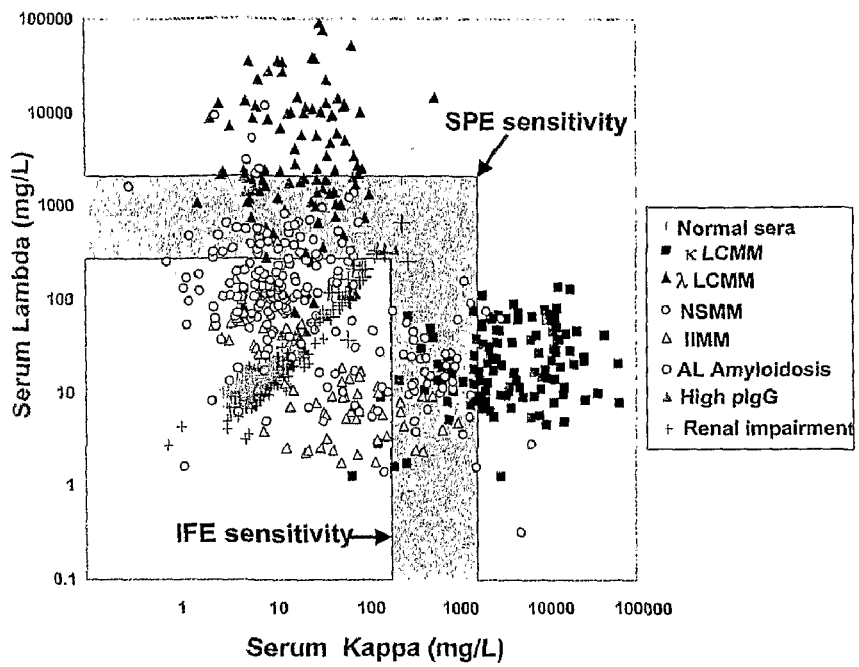
FIG. 3 shows a κ and λ graph of serum free light chains showing samples that would be misidentified as negative using serum protein electrophoresis (SPE) and immunofixation electrophoresis (IFE); LCMM means light chain multiple myeloma; NSMM means non-secretory multiple myeloma; IIMM means intact immunoglobulin multiple myeloma. (Drayson M, Tang L X, Drew R, Mead G P, Carr-Smith H, Bradwell A R. Serum free light-chain measurements for identifying and monitoring patients with Nonsecretory multiple myeloma. *Blood* 2001; 97: 2900-2902; Bradwell A R, Carr-Smith H), Mead G P, Harvey T C, Drayson M T. Serum test assessment of patients with Bence Jones myeloma *Lancet* 2003; 361: 489-491; Mead G P, Carr-Smith H), Drayson M T, Morgan G J, Child J A, Bradwell A R. Serum free light chains for monitoring multiple myeloma. Brit *J. Haematol.* 2004; 126: 348-354; Lachmann H J, Gallimore R, Gillmore J D, Carr-Smith H D, Bradwell A R, Pepys M B, Hawkins P N. Outcome in systemic AL amyloidosis in relation to changes in concentration of circulating free immunoglobulin light chains following chemotherapy. *Brit. J. Haematol.* 2003; 1223: 78-84.)
Figure 4:
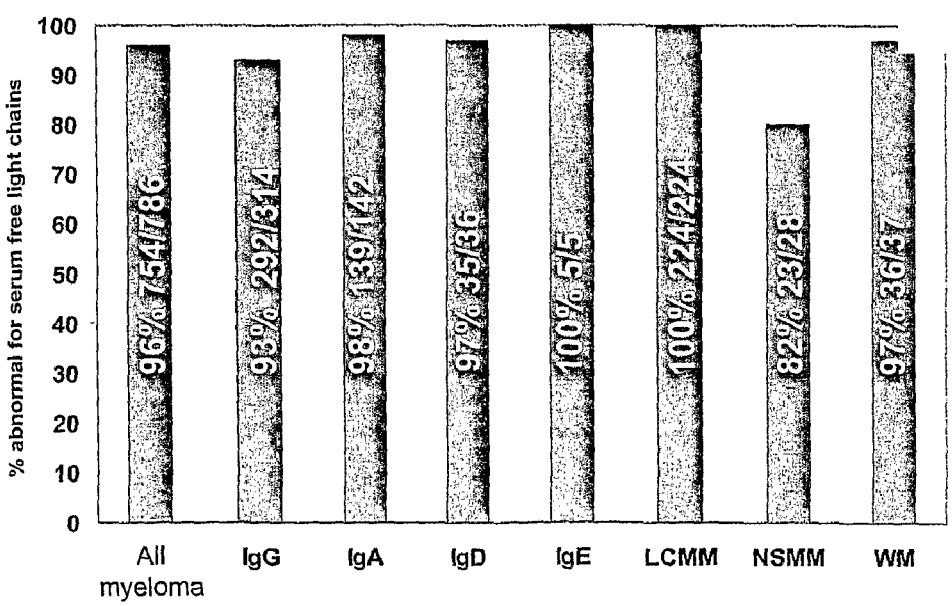
FIG. 4 shows the frequency of abnormal serum free light chain concentrations in patients with different types of multiple myeloma and Waldenström's macroglobulinaemia (WM). LCMM means light chain multiple light chain myeloma; NSMM means non-secretory multiple myeloma. (Drayson M, Tang L X, Drew R, Mead G P, Carr-Smith H, Bradwell A R. Serum free light-chain measurements for identifying and monitoring patients with Nonsecretory multiple myeloma. *Blood* 2001; 97: 2900-2902; Bradwell A R, Carr-Smith H D, Mead G P, Harvey T C, Drayson M T. Serum test assessment of patients with Bence Jones myeloma. *Lancet* 2003; 361: 489-491; Mead G P, Carr-Smith H D, Drayson M T, Morgan G J, Child J A, Bradwell A R. Serum free light chains for monitoring multiple myeloma. *Brit. J. Haematol.* 2004; 126: 348-354.)

DEVELOPMENT AND ANALYSIS OF AN IgA κ/λ ELISA ASSAY SYSTEM FOR THE MONITORING OF MULTIPLE MYELOMA

Introduction

Multiple myeloma (MW is a malignant plasma cell disorder accounting for approximately 10% of haematological malignancies. The disease is characterised by clonal proliferation of plasma cells that produce a monoclonal intact immunoglobulin and/or free light chains (FLC). The monoclonal immunoglobulin is observed in the serum and/or urine of all patients except 1-2% with non-secretory myeloma. Some patients exhibit an increased frequency of monoclonal free light chains. In addition to being used to aid identification of monoclonal gammopathies such as MM, the monoclonal immunoglobulin can be detected and used to monitor the disease. Various methods are currently used to identify and characterise monoclonal immunoglobulins. Serum protein electrophoresis (SPB) and immunofixation electrophoresis (IFE) are two such methods utilised. SPE allows quantitative analysis of monoclonal immunoglobulins, whereas IFE is a qualitative method. More recently FREELITE™ has been developed that allows nephelometric analysis of free light chains. This assay system allows rapid testing of samples in comparison to SPE and IFE and in addition is quantitative, allowing FLC ratios to be calculated. At present no comparable assay system exists to investigate monoclonal light chains attached to heavy chains in MM. This report describes a preliminary assay developed to assess the ability to detect abnormal ratios of monoclonal light chains attached to heavy chains. The assay described is an ELISA assay system for the detection of IgAκ and IgAλ, allowing the quantitation of IgAκ/λ ratios.

FREELITE™ is a trademark of the Binding Site(TBS)Ltd, UK

Methods

Coating of 96 Well Plates with Capture Antibody

Sheep anti-human IgA (TBS product code AU010, affinity purified) was diluted to 5 μg/ml in 1×PBS (pH 7.2) Microtitre plates (High bind, Greiner Bio-one) were coated by the addition of 100 μl of the diluted antiserum to each well. The plates were placed at 4° C. in a humidified atmosphere for 18 hours. The contents of the wells were removed and 110 μl/well of 50% [v/v] Stabilcoat (biomolecular stabiliser/blocking agent) added for 30 minutes to block non-coated regions of the wells. Following removal of the blocking solution, the plates were placed in a vacuum drier for 1 hour. The plates were sealed in foil bags containing desiccant and stored at 4° C.

Determination of the Conjugate Dilution

Sheep anti-human kappa-horseradish peroxidase (HRP), affinity purified or sheep anti-human lambda-HRP, affinity purified were diluted to various dilutions in conjugate diluent (130 nM NaCl, 10% [v/v] HRP conjugate stabiliser, 0.045% [v/v] Proclin 300 (preservative)). Two sheep anti-human IgA coated plates were incubated with IgA controls of known concentration (RID IgA NL control 3.963 mg/ml, RID IgA ML control 0.05 mg/ml and RID IgA UL control 0.18 mg/ml,) diluted 1/50 in Sample Diluent (1×PBS plus 2% [v/v] Stabilguard (biomolecular stabiliser/blocking agent), 1%

[w/v] bovine serum albumin (BSA), 0.05% [v/v] Tween-20, 0.02% [v/v] Kathon (biocide). pH 7.2) for 30 minutes. The plates were washed 3 times with Wash buffer (16×PBS plus 1% [v/v] Tween-20, 0.02% [v/v] Kathon. pH 7.2). One plate was incubated with 100 μl/well of the various dilutions of anti-human kappa-HRP and the second plate with 100 μl/well of anti-human lambda-HRP conjugate of varying dilutions for 30 minutes. The plates were again washed 3 times with Wash buffer and incubated with 100 μl/well of 3,3',5,5' tetramethylbenzidine (TMB) substrate for 30 minutes. The reaction was terminated by the addition of 100 μl/well of 3 M phosphoric acid. Absorbances were measured at 450 nm using a Biotek ELISA plate reader. A conjugate dilution of 1/8000 was chosen for future assays due to it giving the greatest absorbance range for the three IgA assay controls.

Standard Curves of IgAκ and IgAλ

IgAκ and IgAλ sera were used to assess the sensitivity of the IgA ELISA assay in determining IgAκ and IgAλ concentrations. Purified human IgAκ (5.14 mg/ml) and human IgAλ (1.85 mg/ml) sera were serial diluted using tripling dilutions to allow the determination of the detectable concentration range. The ELISA assay method used was as described above. Briefly, IgAκ or IgAλ sera of various dilutions, or IgA controls (as described above) were added to wells at 100 μl/well in duplicate. After washing, either anti-human kappa-HRP (for IgAκ serum plate) or anti-human lambda-HRP (for IgAλ serum plate) conjugate was added, plates incubated and washed, followed by the addition of IMB substrate and 3 M phosphoric acid.

Effect of Competition on the Standard Curves of IgAκ and IgAλ

To assess the effect of the presence of IgAλ on the IgAκ assay and vice versa, serial dilution of IgAλ or IgAκ serum was carried out across an anti-IgA coated plate, whilst IgAκ or IgA$_1$λ serum respectively were serially diluted down the plate. The ELISA method was carried out as described above.

Determination of Rat Ratios of Serum Samples from Healthy Adults

IgAκ and IgAλ values were separately determined, from which κ/λ ratios were calculated. Two sheep anti-human IgA coated plates were incubated with 100 μl/well of IgA controls mentioned previously (diluted 1/800 in Sample Diluent), IgAκ or IgAλ sera of various dilutions, and serum samples from healthy adults diluted 1/4000 in sample diluent for 30 minutes. The plates were washed 3 times with Wash buffer and incubated with 100 μd/well of either anti-human kappa-HRP or anti-human lambda-HRP conjugate at 1/8000 for 30 minutes. The plates were washed 3 times with Wash buffer and incubated with 100 μl/well TMB substrate for 30 minutes. The reaction was terminated by the addition of 100 μl/well of 3 M phosphoric acid. Absorbances were measured at 450 nm using a Biotek ELISA plate reader. Results were analysed using KC4 software.

Determination of κ/λ Ratios of Consecutive Myeloma Patient Serum Samples

The IgAκ and IgAλ assays were carried out as described above, with the addition of myeloma patient serum samples diluted 1/4000 in sample diluent.

Results and Discussion

Standard Curves of IgAκ and IgAλ

The linear detection range of the assays were determined as 0.22-2.2 μg/ml for IgAκ (FIG. 5a) and 0.22-3.2 μg/ml for IgAλ (FIG. 5b). To confirm the concentration range of the standard curves, serial dilutions of the RID IgA NL control were also carried out and assayed. The detectable assay concentration range agreed with those obtained for IgAκ and IgAλ (data not shown). It was concluded that serum samples to be tested would require a 1/4000 dilution to fall within the linear range of the standardised IgAκ and IgAλ curves.

Effect of Competition on the Standard Curves of IgAκ and IgAλ

Studying the effects of competition of IgAλ on the IgAκ assay and vice versa showed IgAλ caused interference to the IgAκ standard curve (leading to a reduction in absorbance) at IgA-concentrations of 1.6 μg/ml and above. IGAc caused interference to the IgA, standard curve at 5.35 μg/ml and above. These findings indicate that the system requires further optimization but all the patient testing reported here was performed at appropriate dilutions to ensure no interference due to competition occurred.

Determination of κ/λ Ratios of Serum Samples from Healthy Adults 18 serum samples from healthy adults, obtained from the Blood Transfusion Services, were assayed in duplicate to determine the normal IgA κ/λ ratios for the ELISA assay. The results indicated a normal range of 0.6 to 1.2. These values were similar to values in the literature stating IgA κ/λ ratios of 0.8 to 1.5 by ELISA (Haraldsson et al., 1991) and 1.1 to 1.8 by nephelometry (Chui et al., 1991).

Determination of κ/λ Ratios of Consecutive Myeloma Patient Serum Samples 99 myeloma patient serum samples were obtained from Dept. Clinical Immunology, University of Birmingham. These serum samples consisted of 10 patient samples sets, following their disease state from presentation, though treatment, and in some cases, into relapse. For most samples, SPE results, FLC κ/λ ratios via FREELITE™ (normal range 0.26-1.65) and total IgA values via nephelometry (normal range 0.7-3.6 g/l) had previously been obtained. IgA κ/λ ratios were obtained in the present study via IgAκ and IgAλ ELISA assays, as described in the methods section. The results obtained, and comparisons to the other methods used to monitor the disease, are discussed below for each patient. In some cases, if discrepancies were observed for results between methods, IFE (Sebia) gels were also produced for disease state clarification.

Patient Number 7148

Figure 6:
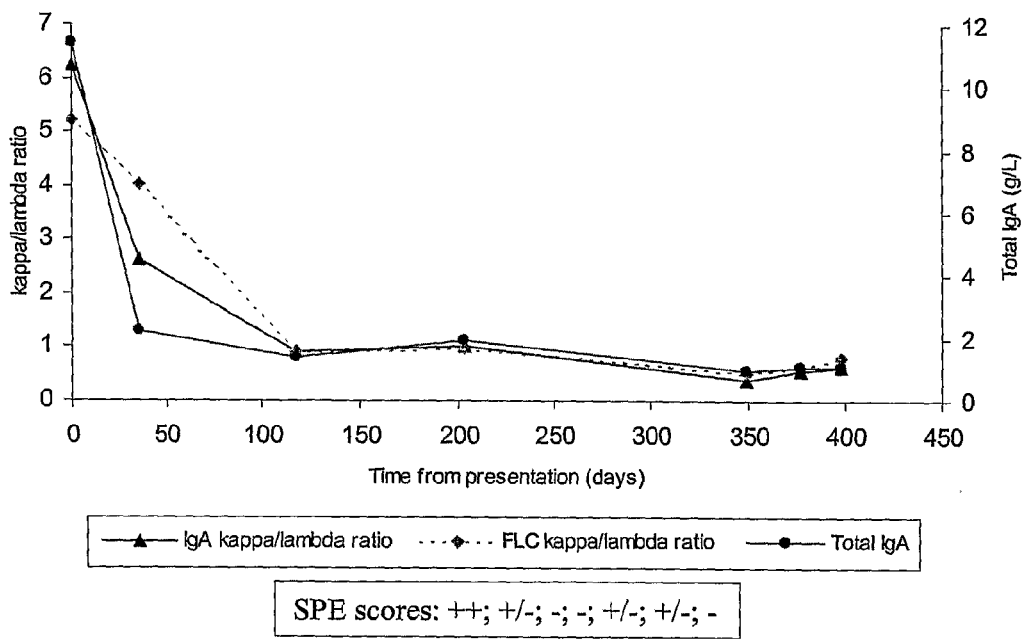
FIGS. 6 to 15 show IgA κ/λ ratio measured by ELISA, as described below (-▲-); κ/λ ratios as determined looking at the free light chains in the sample, not bound to heavy chains (-◆-), and the total IgA in the sample (-●-). SPE scores (Serum Protein Electrophoresis) for each patient for each day on which samples were taken are also presented.

IgA κ/λ ratios produced are in agreement with the trend line observed for FLC κ/λ ratios (FIG. 6). Most of the total IgA values also correlate except for the sample obtained 36 days after presentation, for which the total IgA value was within the normal range, but IgA and FLC κ/λ ratios were elevated, with a SPE score of +/−. IFE of this sample indicated the presence of an IgAκ band. The results for this patient indicate the IgA κ/λ ELISA assays may have similar sensitivity to FREELITE™ and IFE, and may have increased sensitivity with respect to SPE and total IgA values obtained via nephelometry.

Patient Number 7273

Figure 7:
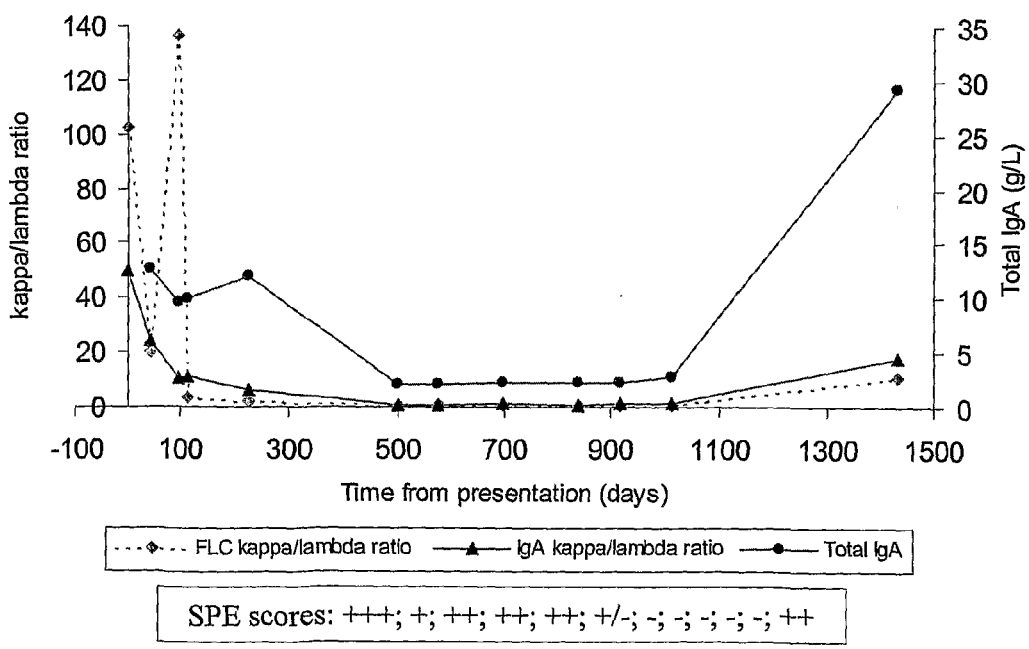

IgA κ/λ ratios calculated agree with trend lines observed for FLC κ/λ ratios and total IgA values FIG. 7). SPE scores correspond to most values obtained by the other methods except for the sample obtained 501 days after presentation. For this sample the SPE score is +/− but values are within normal ranges for all other methods. IFE of this sample indicates no monoclonal bands. These results show IgA κ/λ ELISA assays may be useful when obtaining borderline SPE scores.

Patient Number 7283

Figure 8:
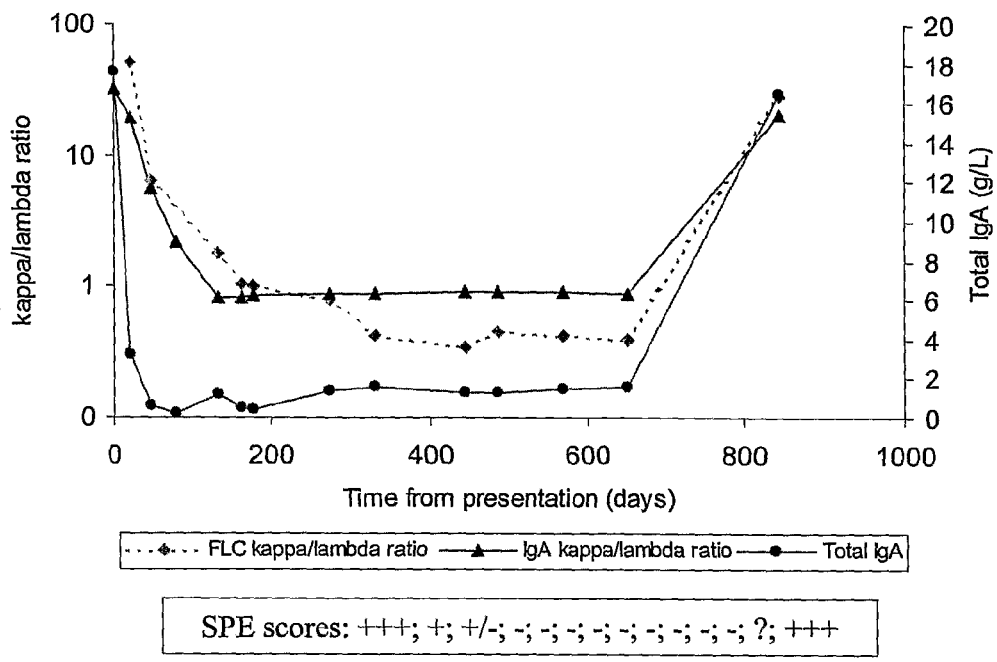

The IgA κ/λ ratios trend line obtained for samples of this patient corresponds to that seen for FLC κ/λ ratios and agree with most of the SPE scores (FIG. 8). The total IgA value is suppressed for the sample obtained 23 days after presentation, although all other results are elevated. For the sample obtained 49 days after presentation, total IgA is suppressed, the SPE score is negative, yet the IgA κ/λ ratio is abnormal. (The FLC κ/λ ratio is not known for this sample). IFE of this sample indicated the presence of an IGAκ band, showing the IgA κ/λ ratio has similar sensitivity to IFE.

Patient Number 7255

Figure 9:
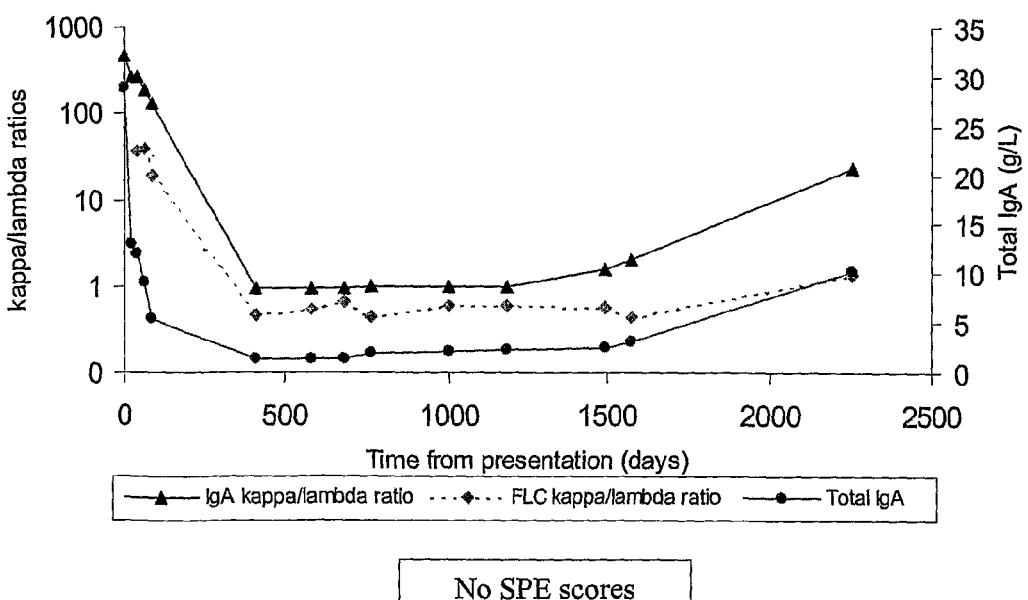

IgA κ/λ ratios agree with most, but not all, of the data obtained using the other detection methods (FIG. 9). No SPE scores have been recorded for these samples. IgA κ/λ ratios are above the normal range for samples obtained 1493, 1576 and 2255 days after presentation. However, total IgA values are within normal range for the first two of these samples and FLC κ/λ ratios are within normal range for all three samples. IFE confirms the presence of a monoclonal IgAκ band in all three samples. Therefore the IgA κ/λ ELISA assays may show greater sensitivity than FREELITE™ for a number of samples.

Patient Number 7401

Figure 10:
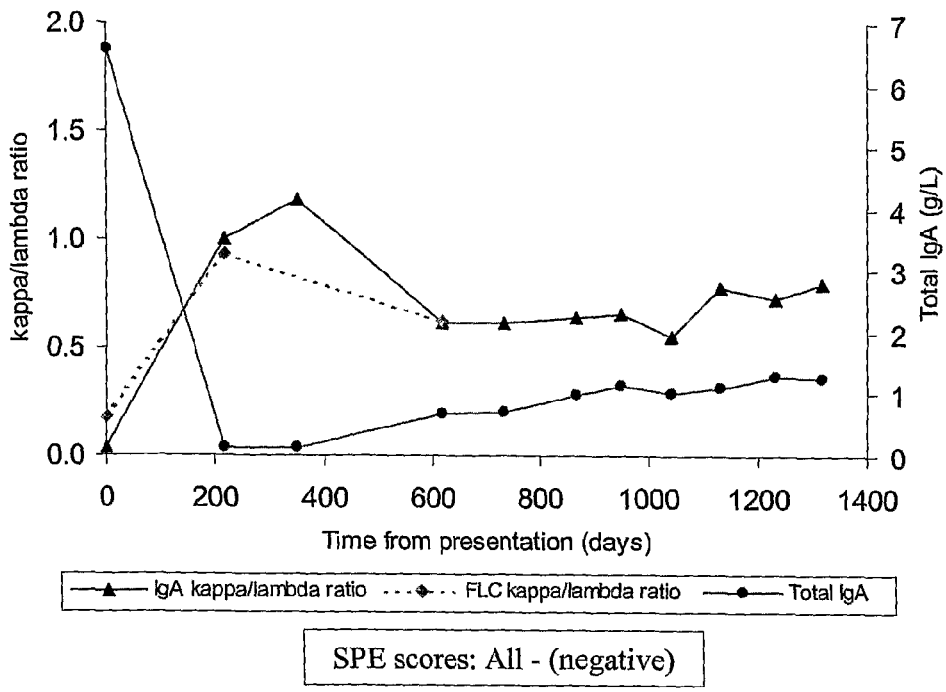

The trend line observed for IgA κ/λ ratios agrees with previously obtained results for FLC κ/λ ratios and total IgA values (FIG. 10). SPE scores were however negative for all samples. IFE confirmed the presence of an IgAλ band upon initial presentation.

Patient Number 70236

Figure 11:
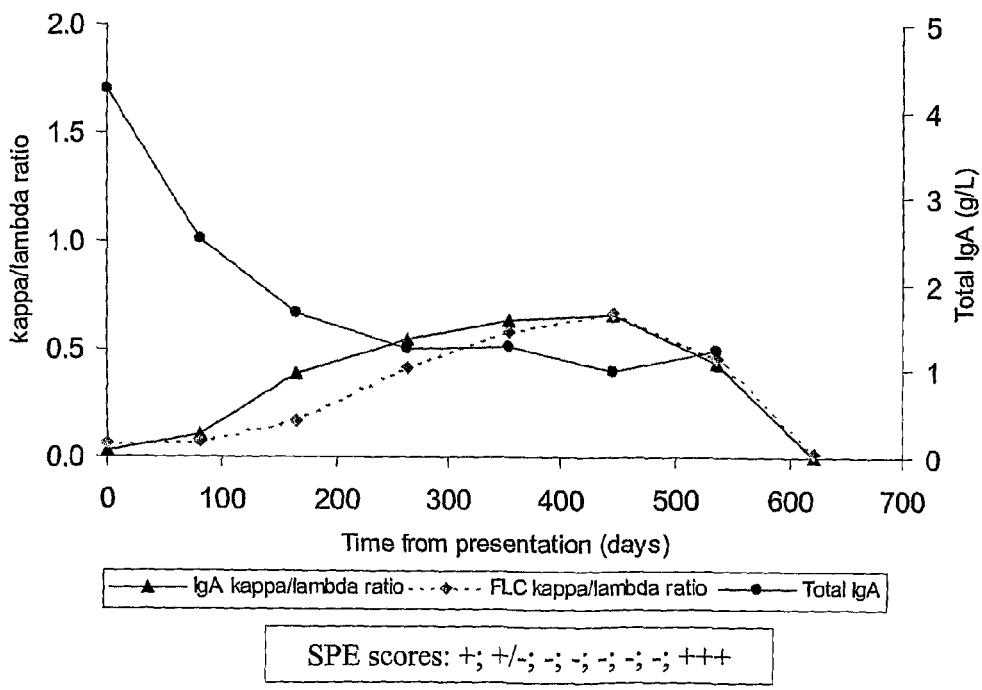

IgA κ/λ ratio and FLC κ/λ ratio trend lines are similar (FIG. 11). However, there are two samples (165 and 263 days after presentation) for which the FLC κ/λ ratios and IgA values are within normal range, SPE scores are negative, but the IgA κ/λ ratios are abnormal. IFE confirms the presence of an IgAλ band. These results suggest in some cases the IgA κ/λ ELISA assays are more sensitive than FREELITE™, total IgA values obtained via nephelometry and SPE, and of equal sensitivity to IFE.

Patient Number 70338

Figure 12:
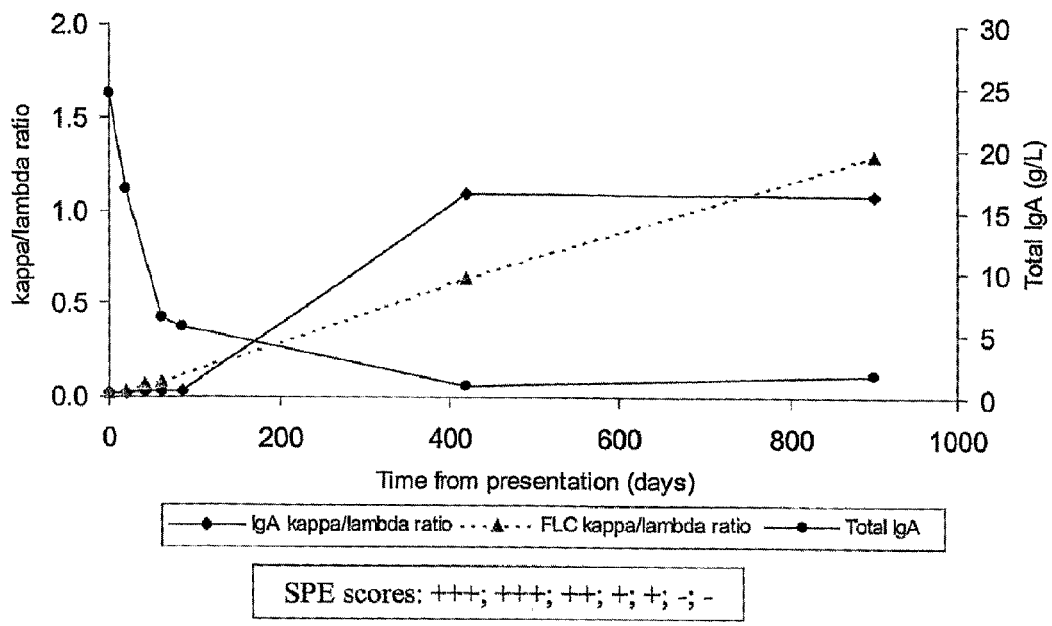

All methods used to investigate the amount of monoclonal immunoglobulin present in the samples gave similar results. The IgAκ/λ ratios produced in the current study agreed with these results (FIG. 12).

Patient Number 70382

Figure 13:
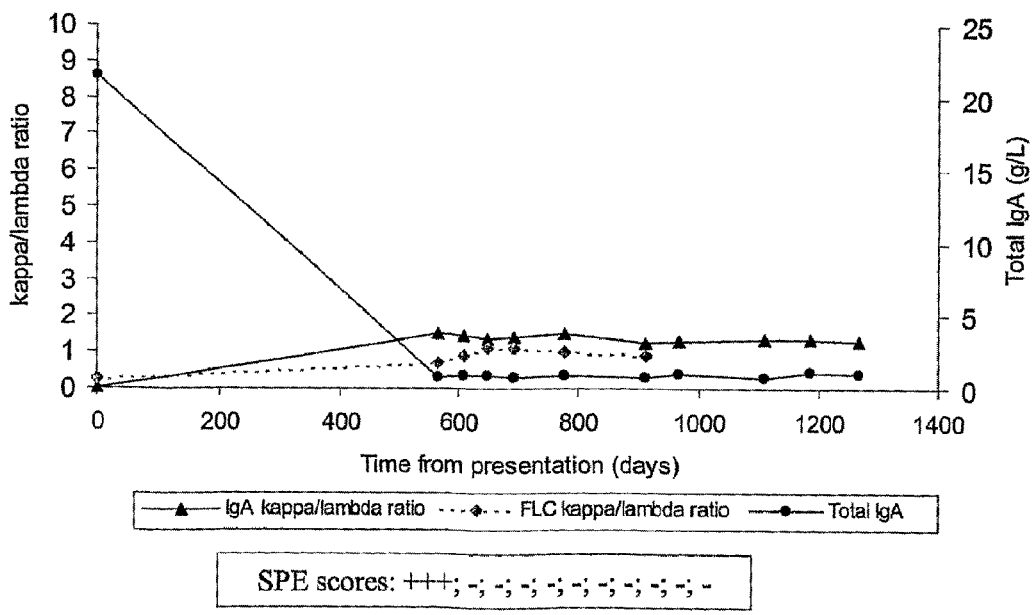

All results correlate with each other. Of note is the FLC ratio upon presentation. This is only just outside the normal range at 0.24, whereas all other methods, including the IgA κ/λ ELISA assays, indicate much greater abnormal levels (FIG. 13).

Patient Number 70392

Figure 14:
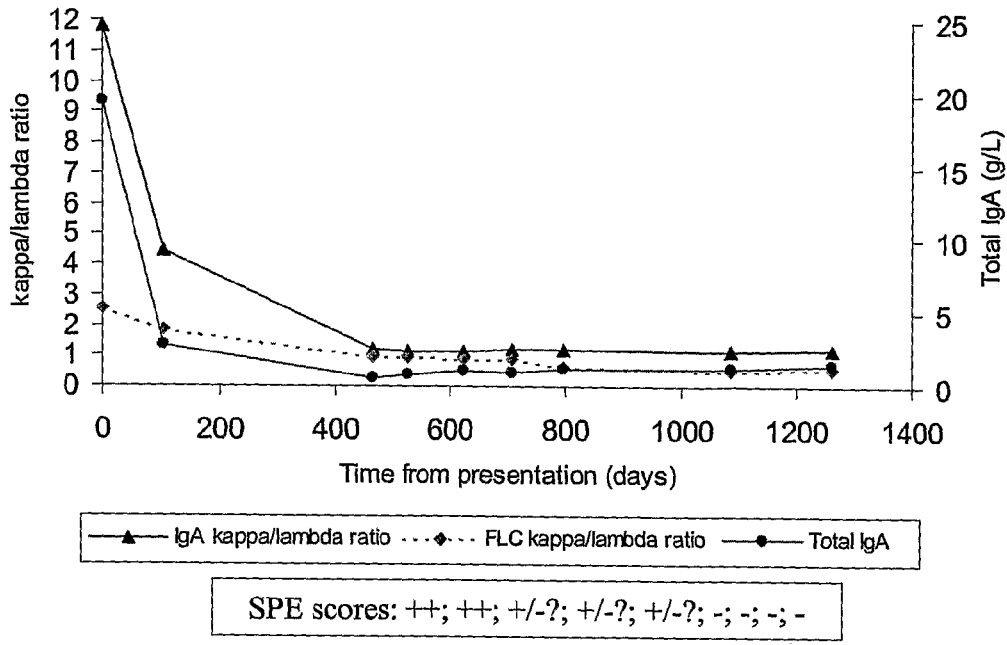

IgA κ/λ ratio and FLC κ/λ ratio trend lines are similar (FIG. 14). However, FLC κ/λ ratios are only just above normal levels upon presentation, whereas IgA κ/λ ratios are highly elevated and agree with all other results.

Patient Number 70052

Figure 15:
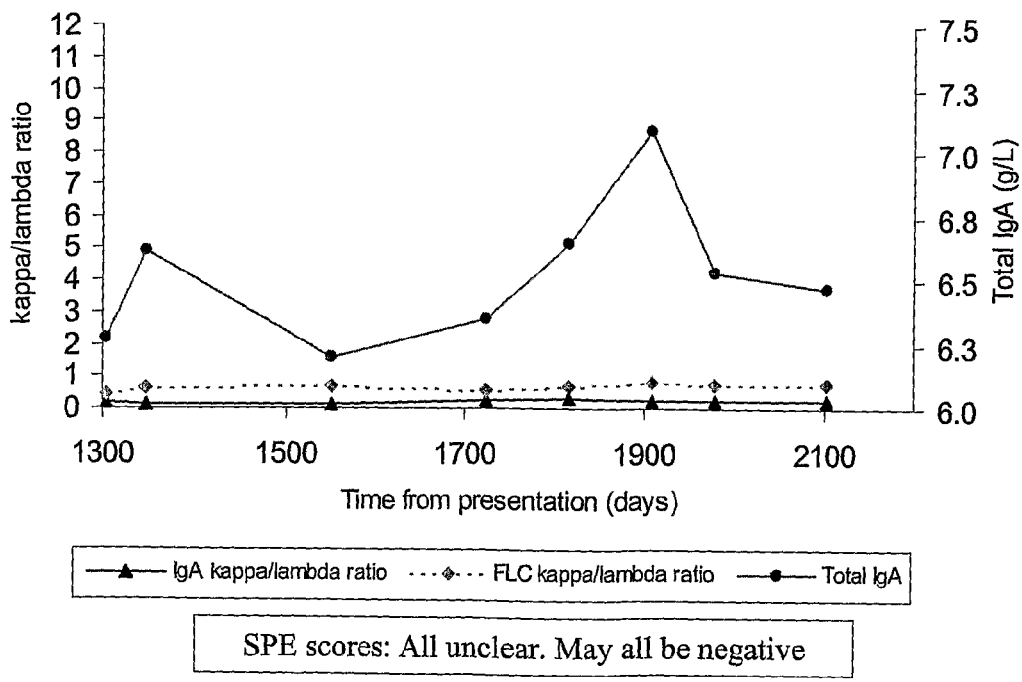

IgA κ/λ ratios are abnormal and agree with values for total IgA. However, SPE scores are unclear, and suggest negative results for all samples. Furthermore, all FLC κ/λ ratios are within the normal range (FIG. 15). IFE for the first four samples confirms the presence of an IgAλ band in these samples. These results suggest this patient may not secrete free light chains and therefore all results are negative with the FREELITE™ assay. They also suggest the IgA κ/λ ELISA assays would be a useful alternative when such a scenario occurs.

In conclusion, for the myeloma patient samples tested, the IgA κ/λ ELISA assays have been shown to be as sensitive as IFE, and in some cases more sensitive than using SPE, FREELITE™ and obtaining total IgA values via nephelometry. There are no incidences in which the IgA κ/λ ELISA assays have been shown to be less sensitive than the other methods. As the majority of the results obtained using the current ELISA based assay system agree with those of the FREELITE™ assay system, it suggests both methods are correctly measuring κ/λ ratios to allow investigation of monoclonal immunoglobulins characteristic of multiple myeloma.

As the field of immuno-diagnostics continues to develop, many may be considering the potential of developing multiplex assay systems that allow the simultaneous characterisation of a large number of analytes. If the use of multiplexing systems becomes more feasible within the clinical environment in future years, it may be possible to adapt the IgA κ/λ ELISA assays described here to allow simultaneous detection of IgAκ and IgAλ in one test sample. This would aid the ultimate challenge of developing a viable multiplex assay system, allowing the simultaneous measurement of various monoclonal immunoglobulins, for use in the diagnosis and monitoring of diseases such as multiple myeloma.

REFERENCES

Haraldsson A, Kock-Jansen M J, Jaminon M, van Eck-Arts P B de Boo T, Weemaes C M, Bakkeren J A. Determination of kappa and lambda light chains in serum immunoglobulins G, A and M. *Ann Clin Biochem* 1991; 28: 461-466

Chui S H. Lain C W. Lewis W H Lai K N. Light-chain ratio of serum IgA1 in IgA nephropathy. *J Clin Immunol* 1991; 11 (4): 219-23

Anti Class—Light Chain Type Antibodies

Polyclonal antibodies against IgGκ were produced using the method substantially as suggested in WO 97/17372. That is, sheep were used to produce the polyclonal antibody.

Sheep were tolerised at day −3 (that is three days before the main immunisation) with 10 mg of IgGλ and IgAκ.

Three days later on day 0, the sheep had the primary immunisation carried out on it with 50 μg of IgGκ. The IgGλ, IgAκ and IgGκ were human immunoglobulins.

Additionally, on day 0, the sheep received anti-human whole λ (100 μg) and sheep anti-human IgA (100 μg). Anti-whole λ binds both bound and free A chains.

On day 42, the sheep had its immunisation boosted with 10 μg of IgGκ. Additionally, it had intravenous administration of sheep anti-human whole λ (100 kg) and sheep anti-human IgA (100 μg).

Finally, on day 49, antibody was collected by plasmaphoresis.

The anti-IgGκ was purified by adsorbing with IgMκ and IgGλ. Excess immune complexes were removed by adding 3% w/v of polyethylene glycol (6,000) and the precipitate was removed by centrifugation.

Positive affinity chromatography was then performed by a passage down an IgGκ column which comprised IgGκ covalently linked to Sepharose 4B. The bound anti-IgGκ antibodies were then eluted from the column with high salt buffer.

Figure 16:
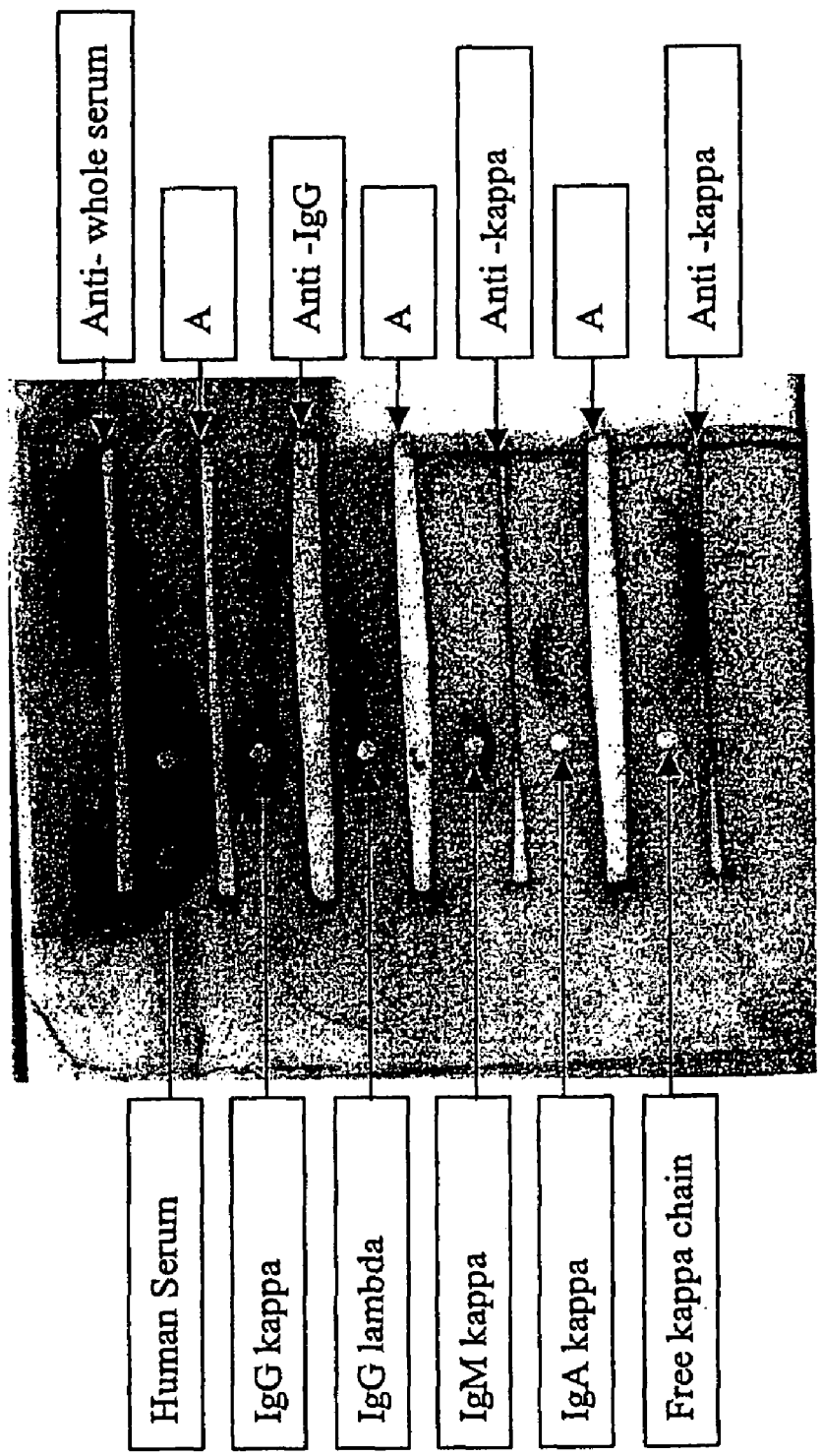
FIG. 16 shows the immunoelectrophoresis (IEP) of anti-IgG-κ (A). The photograph indicates that the antibody reacts well with IgGκ in serum and pure IgGκ. It is also negative against IgGλ and IgMκ and IgAκ. All control antiserum reacted positively with target proteins.

These antibodies were dialysed against a physiological buffer (phosphate buffered saline pH7.4 with preservative)

and concentrated to 1 g/litre. This concentrated solution was then tested by immunoelectrophoresis (IEP) for specificity. The results are shown in FIG. 16.

The production of antibodies was repeated so that antibodies against the junction between heavy and light chains of IgG, and then IgA and IgD were obtained. These were used to identify and quantify intact myeloma immunoglobulins.

Anti-IgGκ Heavy Chain Antibodies:

For antibodies against IgGκ heavy chains, antisera was used nephalometrically to produce a calibration curve.

| Conc (mg/L) | 23.6187 | 47.2375 | 94.475 | 188.95 | 377.9 | 755.8 |
|---|---|---|---|---|---|---|
| Value (Bit) | 519 | 1448 | 3028 | 5660 | 8809 | 12096 |

The calibration curve shape corresponded to the one expected from similar experiments using Freelite.

Known concentrations of different myeloma samples were then tested against the calibration curve, in order to test the efficiency of the antibodies by comparing the sample known concentration to the one given using the nephelometric assay.

The results obtained for the determination of IgGKκ concentrations corresponded to those determined by other methods.

Anti-IgGλ Heavy Chains Antibodies:

For antibodies against IgGλ heavy chains, antisera was used nephalometrically to produce a calibration curve.

| Conc (mg/L) | 23.6187 | 47.2375 | 94.475 | 188.95 | 377.9 | 755.8 |
|---|---|---|---|---|---|---|
| Value (Bit) | 300 | 914 | 1936 | 3105 | 4968 | 7996 |

As before, the calibration curve shape corresponded to the one expected from previous experiments involving nephelometric assay.

The quantity of antibodies was not sufficient enough to proceed with further tests at that time. However, the calibration curve was similar to the one involving the anti-IgGκ antibodies, with expectation of similar results if tested against known concentration samples.

What is claimed is:

1. A method of detecting, monitoring or diagnosing a malignant plasma cell disease in a patient, said method comprising
obtaining a first sample from said patient;
contacting said sample with
(i) an antibody, or a Fab or F(ab')$_2$ fragment thereof, having specificity for a heavy chain class at the same time as having specificity for a first light chain type; in combination with either:
(ii) an antibody, or a Fab or F(ab')$_2$ fragment thereof, having specificity for the heavy chain class at the same time as having specificity for a second light chain type; or
(iii) an antibody, or a Fab or F(ab')$_2$ fragment thereof, having specificity for the heavy chain class and a further antibody, or Fab or F(ab')$_2$ fragment thereof, having specificity for the second light chain, wherein one of said first light chain or second light chain is a λ light chain and the other is a κ light chain;
conducting an immunoassay on said sample to determine a first ratio between the relative amounts of immunoglobulins having a heavy chain class bound to λ light chains, compared to immunoglobulins having the same heavy chain class but bound to κ light chains;
comparing said first ratio to a second ratio, said second ratio comprising the relative amounts of immunoglobins having a heavy chain class bound to λ light chains, compared to immunoglobulins having the same heavy chain class but bound to κ light chains in
a) a sample obtained from an individual without the disease, or
b) a second sample taken from said patient after said first sample,
wherein a deviation of said first ratio from said second ratio indicates the presence of a malignant plasma cell disease and/or the progression/regression of the disease.

2. The method according to claim 1, wherein the binding of the antibodies to the immunoglobulins in the sample is determined by using a nephelometer, a turbidimeter, or flow cytometry.

3. The method according to claim 1, additionally comprising the step of detecting the presence and/or amount of free λ and/or free κ light chains in the sample.

4. The method according to claim 3, wherein the free λ and/or free κ light chains are detected by antibodies specific for free λ or free κ light chains.

5. The method of claim 1 wherein said sample is a blood or serum sample.

6. The method according to claim 1, wherein the heavy chain class antibody, is bound to a bead and flow cytometry is used to determine the kappa/heavy chain to lamda/heavy chain ratios for a given heavy chain class in said sample.

7. A method of detecting, monitoring or diagnosing a malignant plasma cell disease in a patient, said method comprising
obtaining a first sample from said patient;
contacting said sample with
(i) an antibody, or a Fab or F(ab')$_2$ fragment thereof, having specificity for a heavy chain class at the same time as having specificity for a first light chain type; in combination with either:
(ii) an antibody, or a Fab or F(ab')$_2$ fragment thereof, having specificity for the heavy chain class at the same time as having specificity for a second light chain type; or
(iii) an antibody, or a Fab or F(ab')$_2$ fragment thereof, having specificity for the heavy chain class and a further antibody, or Fab or F(ab')$_2$ fragment thereof, having specificity for the second light chain, wherein one of said first light chain or second light chain is a λ light chain and the other is a κ light chain;
conducting an immunoassay on said sample to determine a first ratio between the relative amounts of immunoglobulins having a heavy chain class bound to λ light chains, compared to immunoglobulins having the same heavy chain class but bound to κ light chains;
comparing said first ratio to a threshold value obtained from population data analysis of measured ratios between the amounts of immunoglobulins having a heavy chain class bound to λ light chains, relative to immunoglobulins having the same heavy chain class but bound to κ light chains in samples obtained from individuals without the disease;
wherein a deviation of said first ratio from said threshold value indicates the presence of a malignant plasma cell disease.

* * * * *